(12) United States Patent
Chew et al.

(10) Patent No.: US 9,200,235 B2
(45) Date of Patent: Dec. 1, 2015

(54) METHOD AND APPARATUS FOR ITERATIVE LYSIS AND EXTRACTION OF ALGAE

(71) Applicant: Streamline Automation, LLC, Huntsville, AL (US)

(72) Inventors: Geoffrey Chew, Huntsville, AL (US); Tabitha Boggs, Huntsville, AL (US); H. Waite H. Dykes, Jr., Huntsville, AL (US); Stephen J. Doherty, New Hope, AL (US)

(73) Assignee: Streamline Automation, LLC, Huntsville, AL (US)

( * ) Notice: Subject to any disclaimer, the term of this patent is extended or adjusted under 35 U.S.C. 154(b) by 289 days.

(21) Appl. No.: 13/669,085

(22) Filed: Nov. 5, 2012

(65) Prior Publication Data

US 2013/0072701 A1    Mar. 21, 2013

Related U.S. Application Data

(63) Continuation-in-part of application No. 13/083,895, filed on Apr. 11, 2011, now Pat. No. 8,388,846, and a continuation-in-part of application No. 12/970,484, filed on Dec. 16, 2010, now Pat. No. 8,450,111.

(51) Int. Cl.
| | |
|---|---|
| *B01D 11/02* | (2006.01) |
| *C12N 1/12* | (2006.01) |
| *C11B 1/10* | (2006.01) |
| *C12M 1/00* | (2006.01) |
| *C12N 1/06* | (2006.01) |
| *B01D 11/04* | (2006.01) |

(52) U.S. Cl.
CPC ............... *C11B 1/10* (2013.01); *B01D 11/028* (2013.01); *B01D 11/0288* (2013.01); *C12M 47/06* (2013.01); *C12M 47/10* (2013.01); *C12N 1/06* (2013.01)

(58) Field of Classification Search
CPC .... B01D 11/02; B01D 11/0288; B01D 11/04; B01D 11/0492; Y02E 50/00; Y02E 50/16; Y02E 50/18; C10G 2300/1011; C10G 2300/1014; C10G 1/04; C12N 1/06; C12N 1/12; C12N 2500/76; C12N 2500/70; C12M 47/00; C12M 47/06; C12M 47/10
See application file for complete search history.

(56) References Cited

U.S. PATENT DOCUMENTS

| | | | |
|---|---|---|---|
| 8,211,307 B2 | 7/2012 | Chew et al. | |
| 8,303,818 B2 | 11/2012 | Di Salvo et al. | |
| 2009/0234146 A1 | 9/2009 | Cooney et al. | |
| 2011/0076748 A1* | 3/2011 | Salvo et al. | ............... 435/257.1 |
| 2011/0130551 A1 | 6/2011 | Di Salvo et al. | |
| 2011/0192793 A1 | 8/2011 | Chew et al. | |

FOREIGN PATENT DOCUMENTS

WO    WO 2011163514    * 12/2011

* cited by examiner

*Primary Examiner* — Katherine Zalasky
(74) *Attorney, Agent, or Firm* — Tomas Friend

(57) ABSTRACT

A method and system for processing algae involves the use of an ionic liquid-containing clarified cell lysate to lyse algae cells. The resulting crude cell lysate may be clarified and subsequently used to lyse algae cells. The process may be repeated a number of times before a clarified lysate is separated into lipid and aqueous phases for further processing and/or purification of desired products.

13 Claims, 3 Drawing Sheets

METHOD AND APPARATUS FOR ITERATIVE LYSIS AND EXTRACTION OF ALGAE

CROSS-REFERENCE TO RELATED APPLICATIONS

This application claims priority under 35 U.S.C. 120 to U.S. patent application Ser. No. 13/083,895 filed Apr. 11, 2011, which is a continuation-in-part of U.S. patent application Ser. No. 12/970,512 filed Dec. 16, 2010 and which claims priority to 61/358,322 filed Jun. 24, 2010 and to U.S. patent application Ser. No. 12/970,484 filed Dec. 16, 2010 and which claims priority to U.S. provisional application 61/309,439 filed Mar. 2, 2010. The above related application are incorporated herein by reference in their entirety.

FEDERALLY SPONSORED RESEARCH OR DEVELOPMENT

The United States Government may have certain rights to the invention pursuant to Contract Number DE-SC0001306 awarded by the U.S. Department of Energy.

BACKGROUND OF THE INVENTION

1. Field of the Invention

The present invention relates to methods, systems, and apparatus for lysing and processing algae to extract lipids, proteins, carbohydrates, metabolites, and/or other cellular components. In particular, the invention is a method, system, and apparatus for extracting lipids and other cellular components from algae in which an algae cell lysate comprising an ionic liquid is used to lyse algae.

2. Description of Related Art

US 2009/0234146 A1 discloses a method for the direct transesterification and extraction of biolipids from biomass, including plants, yeast, and algae. The method requires contacting the biomass with a cosolvent comprising an ionic liquid and a polar covalent molecule. The method discloses an example of processing algae cells by suspending freeze dried algae cells in water and mixing the suspension with a cosolvent comprising 46% ionic liquid and 54% methanol by weight. The method requires a cosolvent system containing both ionic liquid and polar covalent solvent to lyse cells and for the formation of separate hydrophilic and hydrophobic phases. The method involves drying algae cells to a powder before suspending the cells in water before lysis.

US 2011/0130551 A1 discloses a one-step process for the lysis of microalgae cells by 1-butyl-3-methylimidazolium chloride (BMIM Cl) and the separation of cellular lipids for use in biofuel production. U.S. Pat. No. 8,211,307 discloses a method for processing algae in which a hydrophilic ionic liquid is used to lyse algae cells, separate hydrophobic and hydrophilic phases are formed, and the two phases are separated. The hydrophilic ionic liquid may be recovered for reuse by adding a salt to the isolated hydrophilic phase to form separate aqueous salt and ionic liquid phases. US 2011/0076748 A1 discloses a method for extracting material from algae cells in which algae cells are contacted with a pure ionic liquid or an active ionic liquid comprising at least 65% ionic liquid. US 2011/0192793 A1 discloses a method for processing algae cells by mixing wet algae cells with a hydrophilic ionic liquid to form a cell lysate and salting out the cell lysate to form separate hydrophobic, ionic liquid, and aqueous salt solution phases.

The aforementioned processes are capable of lysing and processing algae cells using an ionic liquid and recycling the ionic liquid after it is used to lyse cells. Ionic liquids, having lower vapor pressures than volatile organic solvents used for chemical cell lysis, are generally safer to transport and use. Ionic liquids, however, are much more expensive than organic solvents and must therefore be recycled with minimal losses. The process of recycling ionic liquids consumes time and energy and may involve heating the ionic liquid to remove water. Repeatedly heating ionic liquids during recycling may gradually cause some ionic liquids to decompose and/or limit their capacity to lyse cells. Salting out of ionic liquids consumes time and materials and phosphate salts that are effective for salting-out ionic liquids can be damaging to the environment. Accordingly, there is a need for further improved methods and systems for processing algae, and other biomass, that reduce the time, energy, temperature, and materials required for purifying the ionic liquid before reuse.

The formation of separate hydrophobic and hydrophilic phases may be difficult when the volumes of lipid extracted are relatively small compared to the total volume of cell lysate. Accordingly, there is a need for methods and systems for extracting lipid from algae, and other biomass, that improve phase separation.

Accordingly, embodiments of the present invention preferably seek to mitigate, alleviate or eliminate one or more deficiencies, disadvantages or issues in the art, such as the above-identified, singly or in any combination, by providing a system, a method, and a computer-readable medium for processing algae and other biomass, according to the appended patent claims.

BRIEF SUMMARY OF THE INVENTION

The present invention provides a method, system, and computer readable medium for extracting lipids, carbohydrates, proteins, metabolites, small molecules, and/or other components of micro- and macro-algae to produce biofuels, nutrients, pharmaceuticals, chemicals, and/or precursors thereto. The invention is based, in part, on the discovery that a cell lysate formed by mixing an ionic liquid with algae can be used to lyse additional algae after solid debris is removed from the algae lysate. The process involves mixing an IL-containing clarified algae cell lysate with algae cells to form a crude algae cell lysate and removing solid debris from the crude lysate to form a clarified algae cell lysate. The lipid content of the lysate increases with each round of lysis and, after a number of iterations of this process, a clarified cell lysate is allowed or caused to form separate lipid and aqueous phases. The lipid phase is isolated and optionally process to remove residual IL. A fatty acid may be mixed with a clarified lysate to improve phase separation and lipid recovery. Water, methanol, or a water-methanol mixture may be added to a crude or a clarified cell lysate to enhance precipitation of solid debris before removal of solid debris to form a clarified cell lysate. The aqueous phase may be processed to produce purified IL to be reused to begin a subsequent iterative cell lysis process.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DETAILED DESCRIPTION OF THE INVENTION

Figure 1:
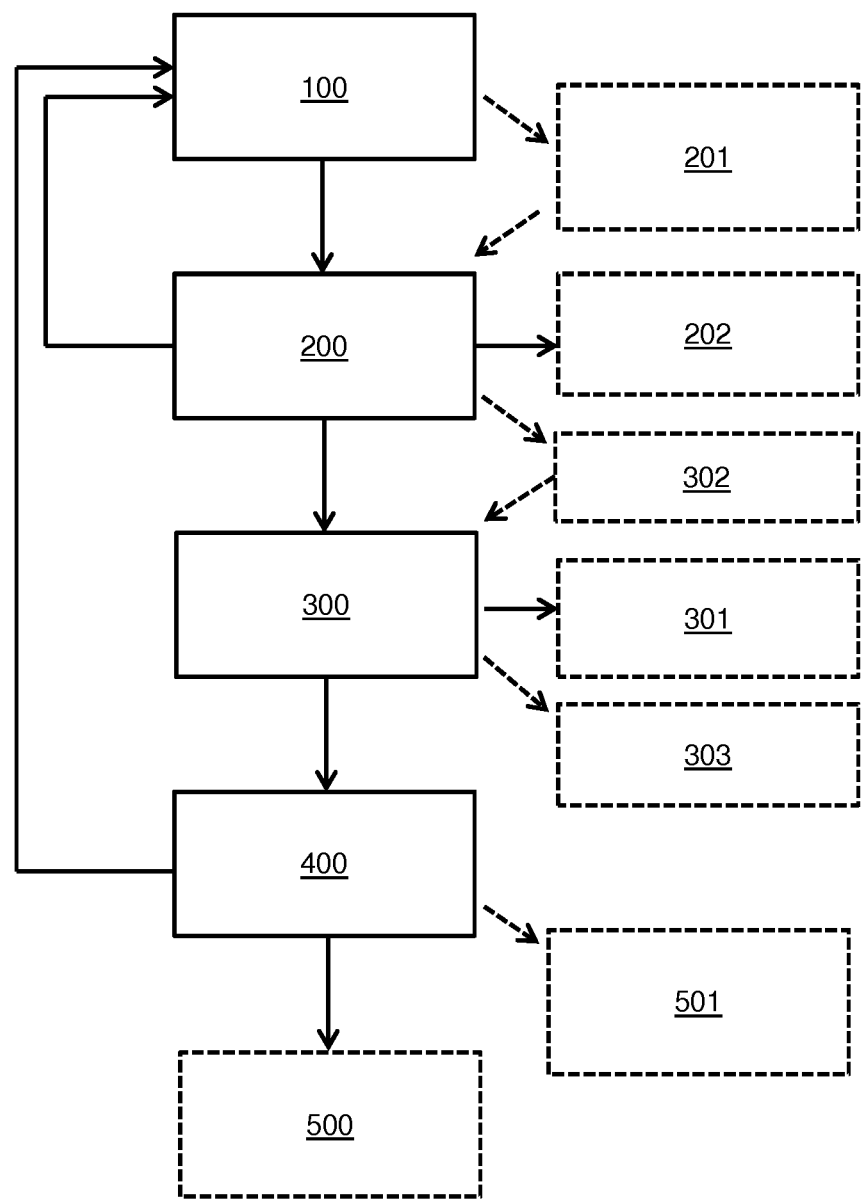
FIG. 1 is a flow diagram of a method according to the invention.

Specific embodiments of the invention are described with reference to the accompanying drawings. This invention may, however, be embodied in many different forms and should not be construed as limited to the embodiments set forth herein. Rather, these embodiments are provided so that this disclosure will be thorough and complete, and will fully convey the scope of the invention to those skilled in the art. In the drawings, like numbers refer to like elements.

The following description focuses on an embodiment of the present invention applicable to the extraction of lipids from algae and in particular to the extraction of triacylglycerols and free fatty acids for the production of biodiesel. However, it will be appreciated that the invention is not limited to this application but may be applied to the extraction many other components of algae cells and even to the extraction of products from non-algae cells that can be lysed using the disclosed method and system.

According to one aspect of the invention, a method is provided in which an IL-containing clarified cell lysate is mixed with algae to lyse algae cells and form a crude IL-containing cell lysate.

According to another aspect of the invention, a method is provided in which sequential batches of algae are mixed with clarified IL-containing cell lysates formed from crude IL-containing lysates of a preceding batch of algae.

According to another aspect of the invention, a method is provided in which a fatty acid is mixed with a clarified IL-containing cell lysate to form separate hydrophilic and hydrophobic phases to be isolated from one another.

According to yet another aspect of the invention, a system for processing algae cells is provided. The system comprises a lysis reactor in fluid communication with solids removal chamber, a liquids separation vessel in fluid communication with the solids removal chamber, and a distillation unit in fluid communication with the liquids separation vessel.

The term "lysis" as used herein with respect to algae cells, involves the dissolution of the cell wall as well as the cell membrane.

An ionic liquid (IL), as used herein, refers to an ionic liquid that is a liquid below 100° C. 1-ethyl-3-methylimidazolium chloride [EMIM]Cl and [BMIM]Cl are examples of ionic liquids having melting temperatures of between 50° C. and 100° C. A preferred IL is a hydrophilic IL that is a liquid at a temperature of below 50° C. 1-ethyl-3-methylimidazolium acetate ([EMIM]Ac), 1-methyl-3-octylimidazolium chloride ([OMIM]Cl), 1-Hexyl-3-methylimidazolium chloride ([HMIM]Cl), 1-Hexyl-3-methylimidazolium iodide ([HMIM]I), and 1-ethyl-3-methylimidazolium triflate ([EMIM]OTf) are examples of preferred ILs. [EMIM]Ac is most preferred.

As used herein, "algae" and "algae cells" refers to fresh water and marine algae, microalgae, and macroalgae. The terms "algae" and "algae cells" may be used interchangeably to indicate algae cells present in a suspension of single celled algae species or cells present in macroalgae. Macroalgae may be chopped, shredded, or whole when lysed. Examples of algae include species of *Amphiprora, Bacillariophyceae, Botryococcus, Chlamydomonas, Chlorella, Chlorococcum, Chlorophyceae, Chrysophyceae, Cylindrotheca, Dunaliella, Laminaria, Nannochloris, Navicula, Neochloris, Phaeodactylum, Pleurochrysis, Prymnesiophyceae, Sargassum, Scenedesmus, Selenastrum, Tetraselmis* sp, and *Thalassiosira*. Examples of species of algae include *Botryococcus braunii, Chlamydomonas reinhardtii, Chlamydomonas moewusii, Chlorella vulgaris, Chlorella pyrenoidosa, Chlorella ellipsoidea, Chlorella vulgaris, Chlorella protothecoides, Dunaliella tertiolecta, Laminaria digitata, Nannochloropsis oculata, Nannochloropsis salina, Neochloris oleoabundans, Phaeodactylum tricornutum, Pleurochrysis carterae, Sargassum muticum, Scenedesmus dimorphus, Selenastrum capricornotum,* and *Thalassiosira pseudonana*. The list of algae provided is provided for illustrative purposes and is not intended to be limiting. The algae being lysed may be from a single strain of algae or a mixture of strains or species, including mixtures of microalgae and macroalgae, for example.

As used herein, a clarified cell lysate is a crude cell lysate that has been clarified by removing solid debris, for example by filtration, centrifugation, and/or removal of solids that settle by gravitation. In some cases, a precipitating agent may be used to enhance precipitation. A crude cell lysate is an unprocessed product of cell lysis.

As used herein, the singular forms "a", "an" and "the" are intended to include the plural forms as well, unless expressly stated otherwise. It will be further understood that the terms "includes," "comprises," "including" and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Method

A flow diagram representing the basic method is shown in FIG. 1 in which solid lines represent required steps and dashed lines represent optional steps. Intact algae cells are mixed with IL-containing clarified algal cell lysate in step 100. The IL-containing clarified algae lysate is originally formed by mixing a substantially pure IL with algae, as described in U.S. Pat. No. 8,211,307, US 2011/0076748, or 2011/0192793 followed by solid debris removal in step 200. The hydrophobic IL may be a single IL or a mixture of ILs. IL is present in the clarified lysate in an amount of at least 65%, preferably 75%, more preferably 85% or 90% by weight. The algae may contain between 5% and 90% extracellular water by weight and is mixed with IL-containing clarified lysate in a ratio of from about 1:5 to 1:20 and more preferably from about 1:10 to about 1:20 by volume. The total amount of water in the mixture of algae and clarified lysate should not exceed about 35%. Mixing is preferably performed at a temperature of between 20° C. and 50° C. but may performed at higher and lower temperatures. A higher temperature may be advantageous, for example, when using an ionic liquid having a melting temperature well above 50° C. A lower temperature may be used, for example, when the ambient temperature and melting point of the ionic liquid are below 20° C. and adequate lysis is achieved at lower temperatures. Mixing takes place for a time sufficient to lyse all intact algae or a target percentage of intact algae. The target may be 99, 98, 95, 90, 85, or 80 percent lysis, for example. Mixing may be achieved by any suitable mixing means including impeller(s), stirring bar(s), paddle mixer(s), and pulse air mixer(s). The minimum duration of mixing depends on the algae, IL, water content, IL content, temperature, and efficiency of mixing and may range, for example, from 1 to 60 minutes.

The crude lysate resulting from the mixed algae and IL-containing clarified lysate normally contains solid algae debris that must be removed in step 200 to generate a clarified lysate that may be used to lyse additional algae. The solid debris may be removed by any suitable means such as filtration, centrifugation, or settling and scraping. Passing the crude lysate through a first filter may advantageously perform the step of removing solid debris and then through a second filter having a finer mesh than the first filter. In some cases, a precipitating agent may be mixed with the crude lysate in step 201 to enhance the formation of solid debris before the solid debris is removed. The precipitating agent may be, for example, an acid or base used to change the pH of the crude lysate. The pH may be selected, for example, to precipitate a product that is to be isolated from the solid debris. Methanol or a methanol-water mixture may also be used as a precipitating agent in a weight ratio of up to 1:1 with the crude lysate. If methanol or methanol/water is used to enhance precipitation, the clarified lysate formed after removal of solid debris in step 200 is not be used for algae lysis in step 100 and is distilled in step 400 to remove methanol and water. A change in temperature may also be used to enhance precipitation. The precipitate, once removed from the crude lysate, may be further processed in step(s) 202 to isolate one or more desired metabolites or macromolecules.

The clarified lysate may be mixed with algae to produce a new crude lysate in step 100 or the clarified lysate may be allowed or caused to form separate hydrophobic and hydrophilic phases in step 300. The hydrophobic (lipid) phase comprises constituents of the algae that are not soluble in the IL-containing aqueous phase. Constituents present in the hydrophobic phase include numerous triacylglycerols (TAGs), which contain fatty acids that may include eicosenioc acid, eicosedienioc acid, arachadonic acid, hexadecadienoic acid, hexadecatrienoic acid, palmitic acid, palmitoleic acid, stearic acid, oleic acid, linoleic acid, and linolenic acid. The aqueous phase comprises water, IL, and water soluble constituents of the lysed algae. The phases may be separated using any suitable separation means, such as sequentially removing the hydrophilic phase and the hydrophobic phase from the bottom of the vessel. After the hydrophobic phase has been isolated, it may be further processed in step(s) 301. For example, TAGs may be isolated and converted into fatty acid methyl esters (FAMEs) for use as biodiesel. In some cases, a free fatty acid may be mixed with the clarified lysate in step 302 to enhance phase formation and separation. For example, oleic acid may be mixed into the clarified lysate before or during the transfer of the clarified lysate to a liquid separation vessel where the clarified lysate rests to allow the formation of separate hydrophobic and hydrophilic phases. Other fatty acids listed above may be alternatively or additionally used to enhance phase formation and separation. The amount of fatty acid mixed with clarified lysate is between 0.5% and 1.5% and preferably around 0.7% by weight of the total clarified cell lysate. In some cases small amounts of IL may be found in the lipid phase and, given the high cost of IL, it may be desirable to recover and reuse this IL. This can be done, for example, by adding a nonpolar solvent to the isolated lipid phase to separate the IL from the lipid phase. The IL may then be recycled to step 100, for example. In some cases a precipitate may form in addition to the hydrophilic and hydrophobic phases. The precipitate may form at the interface of the hydrophilic and hydrophobic phases and/or at the bottom of the vessel. In such cases the precipitate(s) is (are) removed and optionally processed in step 303.

The hydrophilic phase comprising water and IL is distilled in step 400 to separate IL from water. The IL-containing hydrophilic phase is heated to a temperature of above 100° C. and preferably to a temperature of between 110° C. and 120° C. to remove water, which may be condensed in step 500 for recycling or release from the system. If methanol or water/methanol was used as a precipitating agent, the methanol may be recovered together with the water in step 500 or the methanol may be collected separately in step 501. The hydrophilic phase is preferably sparged with air or an inert gas during distillation to disrupt surface tension and increase the liquid surface area and thereby accelerate the distillation process and reduce the distillation temperature and time during which the IL is exposed to elevated temperature.

The cycling of IL-containing clarified lysate through steps 100 and 200 may be repeated a limited number of times. For example, steps 100 and 200 may be cycled 2 times, 5 times, 10 times, 20 times 30 times, 40 times, or 50 times. The clarified lysate, however, contains a higher proportion of water with each cycle. At some point, the combined water in the algae being lysed and the water in the clarified lysate will reach 35%, which results in diminished algae lysis. Therefore, the clarified lysate must be passed onto step 300 before the threshold of 35% combined total water in the lysing mixture is reached. Accordingly, algae cell suspension or macroalgae comprising less water allow the clarified IL-containing lysate to be used for more cycles of lysis than algae comprising more water. The number of cycles though steps 100 and 200 may also be limited by the efficiency of extraction. The optimum number of cycles before moving to liquid separation step 300 may be determined experimentally by comparing the amount of desired product extracted after each cycle. For example, if the desired product is TAG, steps 100 and 200 may be repeated for a number of cycles with a small aliquot taken after each cycle. Each sample may be analyzed to determine the amount of desired product in the sample. The amount of desired product should increase with each cycle in proportion with the amount of algae being lysed. The number of cycles at which the increase in amount of desired product does not increase in relative proportion to the amount of algae lysed minus 1, for example, may be selected as the number of times to cycle between steps 100 and 200. Recovering the IL by distilling away water does not appear to diminish the ability of the IL to lyse algae. For example, [EMIM]Ac recycled through 50 rounds of dewatering by distillation maintains lysing activity. Water may alternatively be removed from the IL-containing hydrophilic phase by heating with passive or active solar heat, microwaves, or heat from combustion without recover of water.

The above method has been demonstrated using [EMIM]Ac or [EMIM]OTf with *Tetraselmis* sp., *Chlorella pyrenoidosa, Chlorella ellipsoidea, Chlorella vulgaris, Laminaria digitata, Nannochloropsis oculata, Sargassum muticum*, and *Scenedesmus dimorphus*.

System

Figure 2:
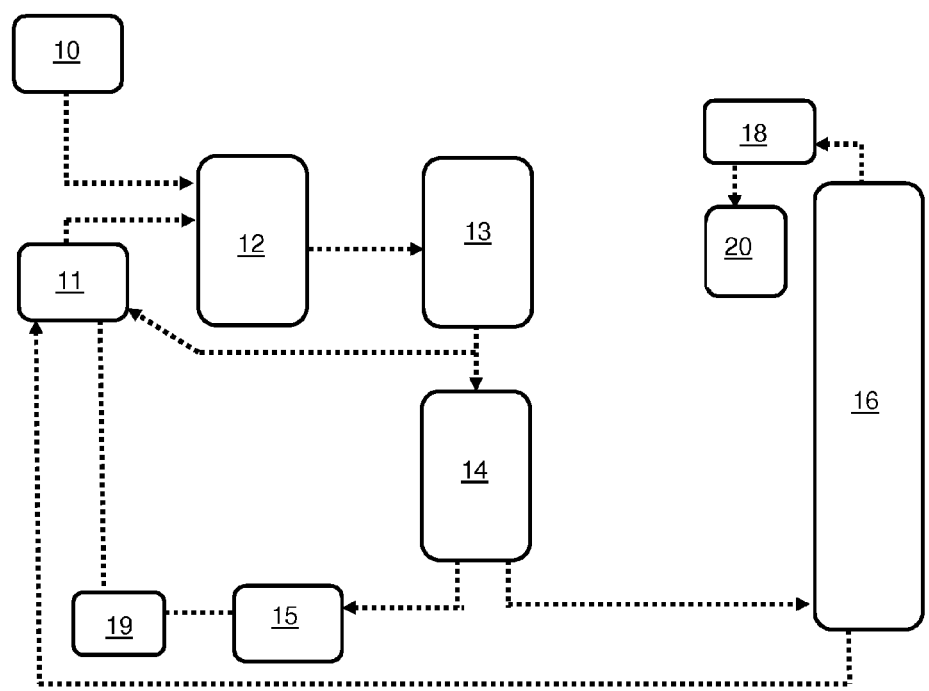
FIG. 2 is a schematic of a general system according to the invention.

A generalized system for performing the method of the invention is shown in FIG. 2. A source of algae 10 and a source of IL-containing clarified algal cell lysate 11 are in communication with a lysis reactor 12. The lysis reactor 12 comprises means for mixing the algae and clarified lysate and is in fluid communication with a solids removal chamber 13. Crude lysate formed in the lysis reactor 12 are transferred to the solids removal chamber 13 where solids debris is removed from the crude lysate to form a clarified lysate. Solids removal chamber 13 may comprise, for example, a prefilter having a first mesh size and a filter having a smaller mesh than the prefilter. Solids removal chamber 13 may be a centrifuge or any other suitable means for removing solid debris from a cell lysate. Clarified lysate may be transferred back to the lysis reaction chamber to be mixed with algae cells to produce a new crude cell lysate or the clarified cell lysate may be transferred to liquid separation vessel 14 where lipid containing hydrophobic and IL-containing hydrophilic phases separate from one another. The lipid containing hydrophobic phase is transferred for removal from the system or optionally for further processing to lipid collection port 15. Residual IL may optionally be recovered from the lipid by IL recovery unit 19. The IL-containing hydrophilic phase is transferred from the liquid separation vessel 14 to distillation unit 16 where it is heated, for example, to between 110° C. and 120° C. to remove water that may be condensed by condenser 18 and removed from the system or recycled via water container 20.

Example

Figure 3:
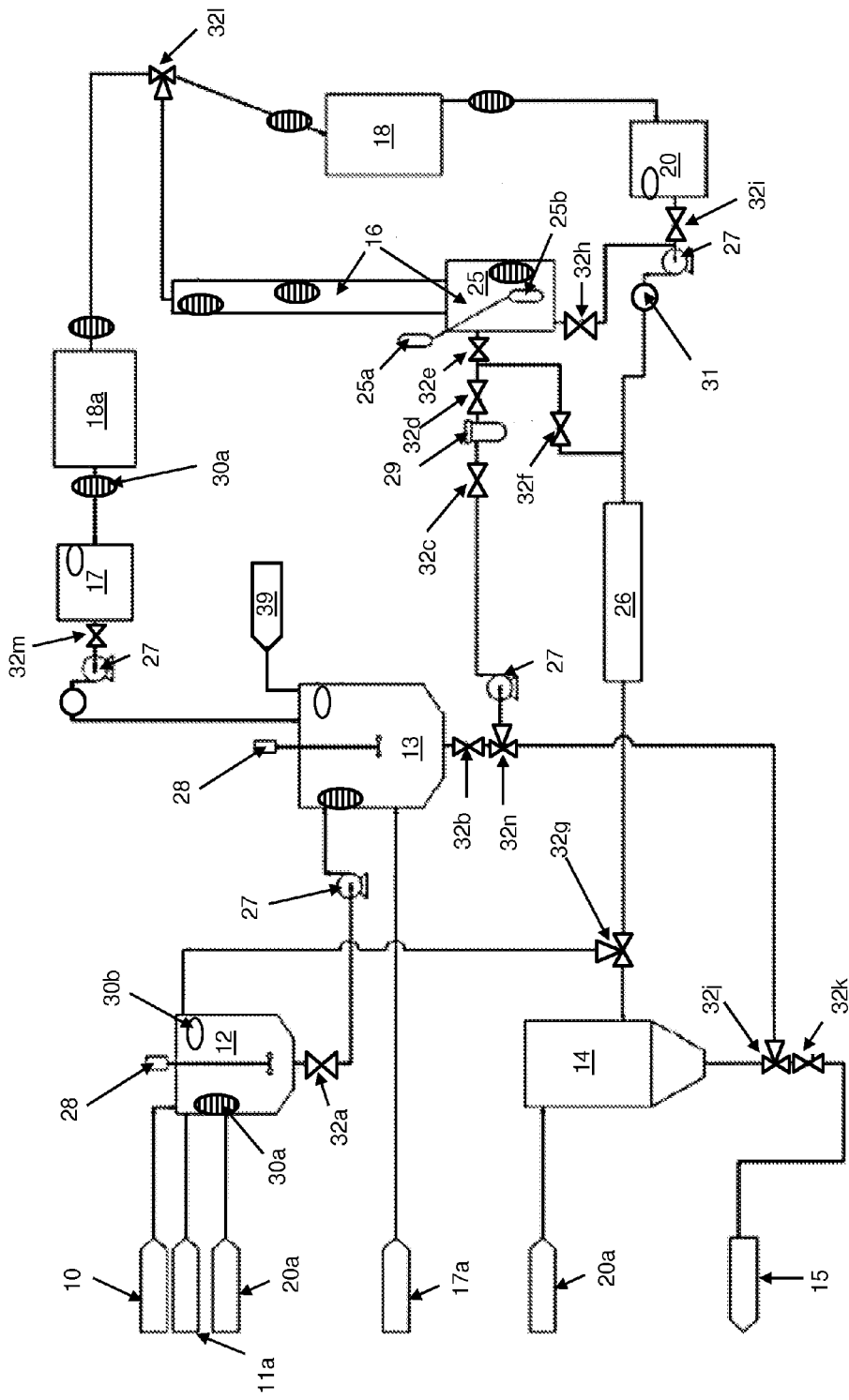
FIG. 3 is a schematic of a specific embodiment of a system according to the invention.

FIG. 3 shows an embodiment of a system for performing an algae processing method according to the invention. A lysis reactor 12 is configured to receive algae from a source of algae 10 and to receive an IL-containing clarified algae cell lysate from a solids separation chamber 13 via valves 32*b* and 32*n*, pump 27, valve 32*c*, filter 29, valves 32*d* and 32*f*, optionally in-line mixer 26, and valve 32*g*. At start-up, no algae has been lysed and there is no IL-containing clarified lysate so lysis reactor 12 is configured to receive a substantially pure IL from a source of IL 11*a* and to receive water from water source 20*a*. Lysis reactor 12 is equipped with a means for mixing algae with IL or IL-containing clarified algae lysate. The mixing means may be an impeller and shown or any other suitable mixing means. Lysis reactor 12 is also provided with a temperature sensor 30*a* and a level sensor 30*b*.

A solid separation chamber 13, in this case a prefilter, is configured to receive crude cell lysate from lysis reactor 12 via valve 32*a* and pump 27 and to remove solid debris from crude cell lysate to produce a clarified algae cell lysate. A stirrer 28 circulated liquid in the chamber to direct solids toward the sides of the chamber to minimize clogging of a mesh filter (not shown) at the bottom of the chamber. The solid separation chamber 13 is configured to deliver a clarified algae cell lysate to either lysis reactor 12 or separation vessel 14 via valves 32*b* and 32*n*, pump 27, valve 32*c*, filter 29, valves 32*d* and 32*f*, optionally in-line mixer 26, and valve 32*g*. Liquid separation vessel 14 is configured to receive clarified algae cell lysate from solid separation chamber 13, for the formation of separate lipid-containing hydrophobic and IL-containing hydrophilic phases, and for the isolation of the hydrophilic and hydrophobic phases from one another. The liquid separator 14 in this embodiment is configured similarly to a separatory funnel such that a lower hydrophilic phase may be removed from the bottom of the vessel and transferred to distillation unit 16 via valves 32*j* and 32*n*, pump 27, valve 32*c*, filter 29, and valves 32*d* and 32*e*. After the IL-containing hydrophilic phase is removed from liquid separation vessel 14, the lipid-containing hydrophobic phase is removed through valves 32*j* and 32*k* and transferred to lipid collection port 15, which may be connected, for example, to a storage container or pipeline (not shown).

The embodiment shown in FIG. 3 comprises an optional reservoir 17 containing an optional precipitating agent, in this case methanol. A precipitating agent may be used, for example, after a number of lysis cycles and before transfer of clarified cell lysate to the liquid separation vessel 14. In this example, methanol is pumped out of reservoir 17 through valve 32*m* by pump 27, through a flow meter 30, and into solid separation chamber 13. Stirrer 28 is used to mix the precipitating agent with the crude lysate. The methanol precipitating agent separates with the hydrophilic phase in liquid separation vessel 14 and is transferred to the distillation unit in the hydrophilic phase.

The distillation unit 16 comprises a sparger 25 that introduces compressed air from a compressed air source 25*a* to a sparging outlet 25*b* in the sparger. Temperature sensors 30*a* monitor the temperature at various locations in the distillation unit. Methanol, having a lower boiling point than water comes off the distillation apparatus first and is directed through valve 32*l* to condenser 18*a* which, in turn, flows into reservoir 17. Temperature sensors 30*a* monitor temperatures before and after the condenser. Water (steam) comes off the distillation apparatus after methanol and is directed through valve 32*l* to condenser 18 which, in turn, flows into water reservoir 20. Water may be returned to the lysis reactor via valve 32*i* through a pump 27, a flow meter 31, optionally through in-line mixer 26, and valve 32*g*. Supplemental water and methanol may be provided from supplemental water supplies 20*a* and supplemental methanol supply 17*a*.

A source of fatty acid 39, in this case oleic acid, is configured to deliver oleic acid into the solid separation chamber 13. Fatty acid is introduced after multiple rounds of lysis and, for example, immediately before the clarified lysate is transferred to liquid separation vessel 14 via valves 32*b* and 32*n*, a pump 27, valve 32*c*, filter 29, valve 32*f*, in-line mixer 26, and valve 32*g*. In-line mixer 26 is used to ensure that the fatty acid is completely mixed with the clarified cell lysate before the clarified lysate reached the liquid separation vessel 14. Valves 32*c* and 3*d* facilitate changing filter 29. Flow meters 31, pumps 27, pressure sensors, temperature sensors 30*a*, and level sensors 30*b* may be located at any number of positions within the system in addition to or as an alternative to the positions shown in FIG. 3. The fatty acid may alternatively be added to and mixed with the clarified cell lysate at any point between the solid removal chamber 13 and the liquid separation vessel 14.

The present invention is described using lipid extraction as an example. One will appreciate that the present invention can also be used to extract a component found in the lipid phase, solid precipitate (solid debris), or the hydrophilic phase of the clarified cell lysate. Thus, the method and system may be used to process algae for the purpose of extracting other materials from algae, including polysaccharides, sugars, xanthophylls and other carotenoids, nucleic acids, proteins, and omega-fatty acids. Lipid soluble products may be isolated from the lipid phase recovered from the liquids separation vessel using techniques known in the art. Insoluble products or products made insoluble by a precipitating agent in the solids removal chamber may be isolated from the precipitated solid using techniques known in the art. Products found in the hydrophilic phase of the clarified cell lysate may be extracted using extraction methods known in the art.

Embodiments of the present invention are described herein with reference to a flowchart diagram. It will be understood that some or all of the illustrated blocks may be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. Valves, sensors, pumps, meters, the distillation unit, chambers, reactor, vessels, and heating may all be controlled by microprocessor or computer controller. Computer readable code may be stored on a tangible computer readable medium and used to control the operation of the system and performance of the method. Any suitable computer readable medium may be utilized including hard disks, CD-ROMs, optical storage devices, a transmission media such as those supporting the Internet or an intranet, or magnetic storage devices.

The invention has been described with reference to a limited number of preferred embodiments. One of skill in the art will readily appreciate that the number of described embodiments is limited for the sake of brevity and clarity and that the invention is not limited to the embodiments described. Many other embodiments may be substituted for those described herein without departing from the spirit and scope of the invention.

What is claimed is:

1. A method for processing algae cells comprising:
   a) mixing algae cells with a first clarified algal cell lysate to form a crude algal cell lysate, said first clarified algal cell lysate comprising an ionic liquid;
   b) removing solid debris from said crude algal cell lysate to form a second clarified algal cell lysate;
   c) forming separate lipid-containing hydrophobic and ionic liquid-containing hydrophilic phases in the second clarified algal cell lysate; and
   d) isolating the lipid-containing hydrophobic phase from the ionic liquid-containing hydrophilic phase;
   wherein the first and second clarified algal cell lysates each comprise at least 65% hydrophilic ionic liquid by weight and
   wherein a total amount of water in the crude algal cell lysate formed in step a) is not more than 35% by weight.

2. The method of claim 1, and further comprising removing water from the algae cells before mixing with the first clarified algal cell lysate.

3. The method of claim 1, and further comprising mixing a fatty acid with the second clarified algal cell lysate before forming separate lipid-containing hydrophobic and ionic liquid-containing hydrophilic phases.

4. The method of claim 3, wherein said fatty acid is added in an amount of at least 0.7% of the second clarified algal cell lysate by weight.

5. The method of claim 1, wherein algae cells and first clarified algal cell lysate are mixed in a weight ratio of between 1:5 and 1:20.

6. The method of claim 1, wherein said mixing of algae cells and first clarified algal cell lysate is performed at a temperature of between 20° C. and 50° C. for a duration of between 1 and 60 minutes.

7. The method of claim 1, and further comprising mixing the crude algal cell lysate with a precipitating agent before said removing solid debris.

8. The method of claim 7, wherein said precipitating agent is selected from the group consisting of an acid, a base, methanol, and 50% methanol in water.

9. The method of claim 1, wherein the algae cells are in the form of an algae cell suspension comprising between 10% and 90% water by weight.

10. The method of claim 1, wherein the algae cells are in the form of whole, shredded, or chopped macroalgae.

11. The method of claim 1, wherein the ionic liquid is selected from the group consisting of 1-ethyl-3-methylimidazolium chloride, 1-butyl-3-methylimidazolium chloride, 1-ethyl-3-methylimidazolium acetate, 1-methyl-3-octylimidazolium chloride, 1-Hexyl-3-methylimidazolium chloride, 1-Hexyl-3-methylimidazolium iodide, 1-ethyl-3-methylimidazolium triflate, and combinations thereof.

12. The method of claim 1, and further comprising repeating a cycle of steps a) and b) before proceeding to step c).

13. The method of claim 12, wherein said repeating the cycle of steps a) and b) is performed between 2 and 50 times before proceeding to step c).

* * * * *